United States Patent
Band et al.

[11] Patent Number: 5,167,621
[45] Date of Patent: Dec. 1, 1992

[54] FLUID EXTRACTORS

[75] Inventors: David M. Band, Surbiton; David G. Penman, London, both of England

[73] Assignee: Surgicraft Limited, Redditch, United Kingdom

[21] Appl. No.: 720,805

[22] PCT Filed: Jan. 23, 1990

[86] PCT No.: PCT/GB90/00093

§ 371 Date: Sep. 23, 1991

§ 102(e) Date: Sep. 23, 1991

[87] PCT Pub. No.: WO90/08560

PCT Pub. Date: Aug. 9, 1990

[30] Foreign Application Priority Data

Jan. 26, 1989 [GB] United Kingdom ............... 8901692

[51] Int. Cl.$^5$ ............................................. A61M 1/00
[52] U.S. Cl. ............................................. 604/35; 604/319
[58] Field of Search ................ 604/319, 4, 181, 35, 604/321, 118

[56] References Cited

U.S. PATENT DOCUMENTS

| | | | |
|---|---|---|---|
| 4,033,345 | 7/1977 | Sorenson et al. | 604/4 |
| 4,655,740 | 4/1987 | Ruhland | 604/319 |
| 4,787,894 | 11/1988 | Turnbull | 604/319 |
| 4,813,931 | 3/1989 | Hauze | 604/319 |
| 4,870,975 | 10/1989 | Cronk et al. | 604/319 |
| 4,950,247 | 8/1990 | Rosenblatt | 604/319 |
| 4,995,123 | 11/1990 | May | 604/133 |
| 5,024,613 | 6/1991 | Vasconcellos et al. | 604/319 |

*Primary Examiner*—Paul J. Hirsch
*Attorney, Agent, or Firm*—Trexler, Bushnell, Giangiorgi & Blackstone, Ltd.

[57] ABSTRACT

Applying suction to the mouthpiece (22) of the fluid extractor creates suction in the uppermost compartment (10) and distends the elastic diaphragm (13) upwardly, which creates suction in the second compartment (11) to cause the suction valve (15) to open and creates suction in the lowermost compartment (12) and in the suction tube (19), whereby mucus from a patient (e.g., a new-born baby) can be drawn through the suction tube (19) into the lowermost compartment (12) as the diaphragm (13) is self-restoring to neutral position, repeated sucking and releasing of the mouthpiece (22) results in a build-up and maintenance of reduced pressure in the lowermost compartment (12) to continue drawing fluid from the patient and discharging of it into that compartment, while the elastic diaphragm (13) also provides a barrier between the mucus and the users mouth and between the users breath and the patient.

13 Claims, 2 Drawing Sheets

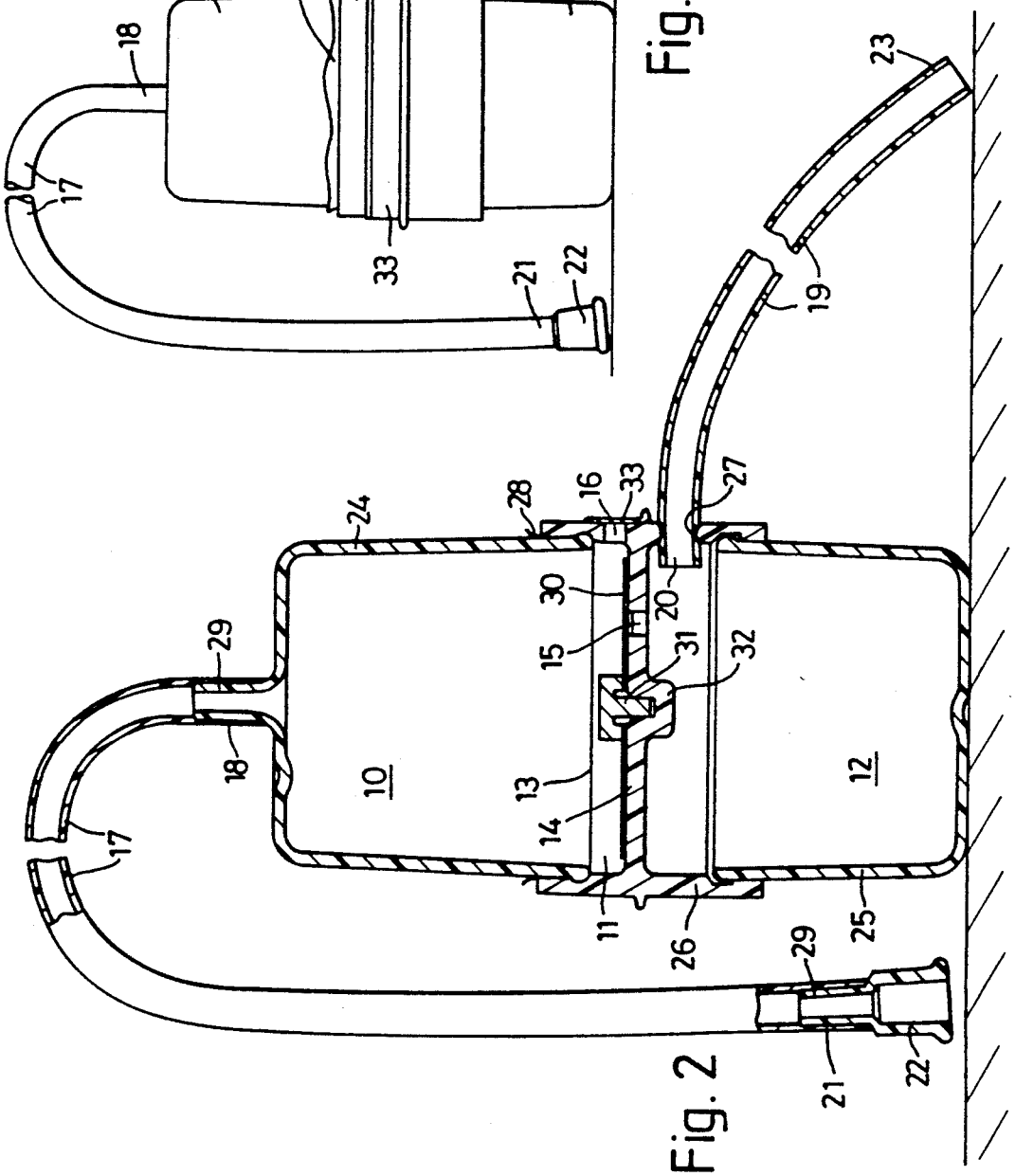

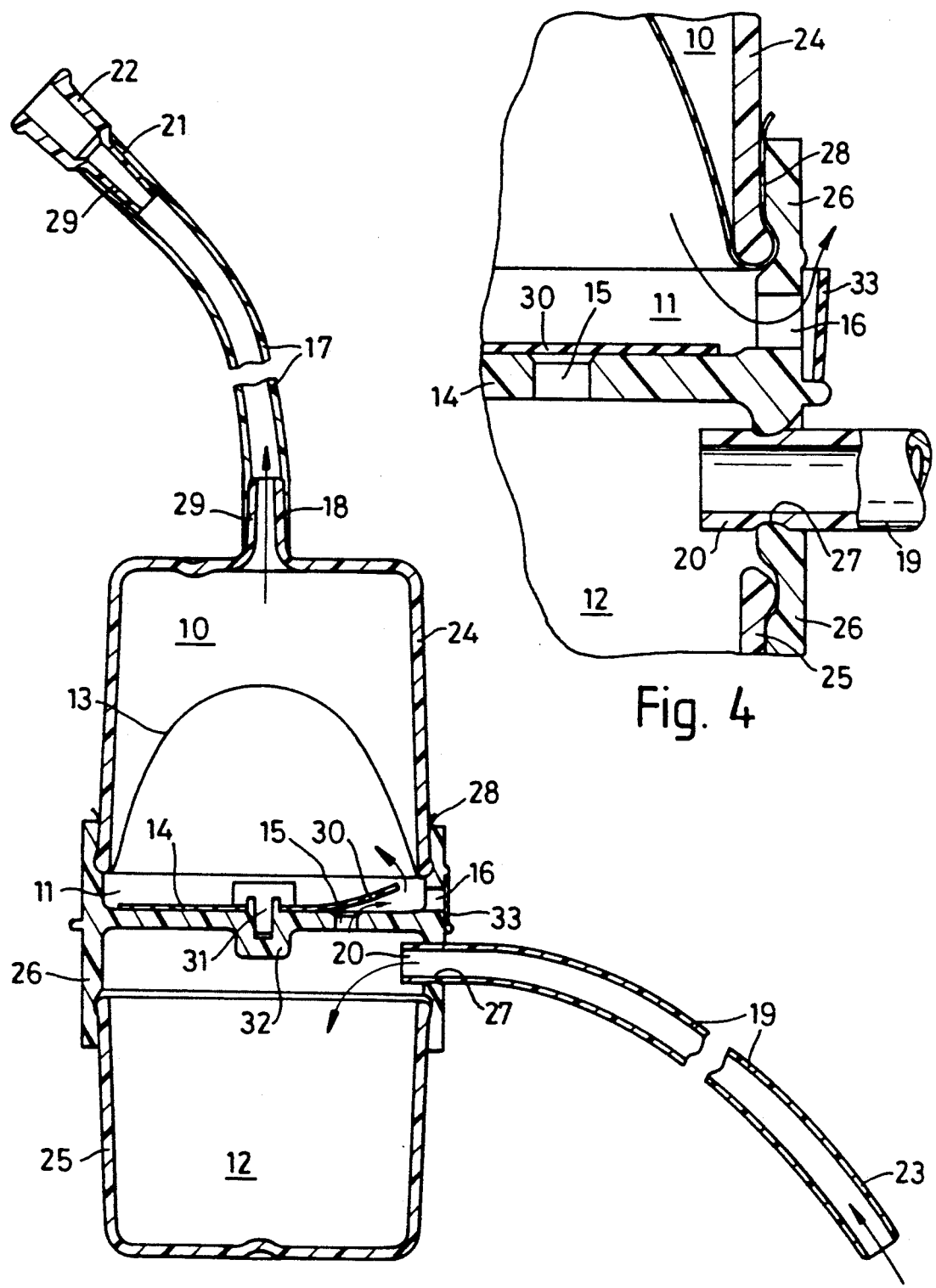

FLUID EXTRACTORS

This invention relates to fluid extractors, e.g., for extracting and collecting mucus from a patient, and has for its object the provision of an extractor readily operated merely by a physical sucking action while ensuring patient and user isolation, with minimal need of handling, and completely or partially disposable.

According to the present invention, a fluid extractor comprises at least three closed compartments in vertical succession, the uppermost compartment being separated from a second compartment by an elastic diaphragm, the second compartment being separated from the lowermost compartment by a partition containing a first non-return valve closed to air flow from the second compartment to the lowermost compartment, a second non-return valve closed to air flow from the atmosphere to the second compartment, a first flexible tube communicating at one end with the upper region of the uppermost compartment, and a second flexible tube communicating at one end with the upper region of the lowermost compartment, the diaphragm being distended upwards by suction, applied by mount to the remote end of the first flexible tube and through that tube to the uppermost compartment, from a neutral state to which it returns when the suction is released.

Thus, with the user's mouth holding the remote end of the first flexible tube—which preferably has a mouthpiece—the extractor will hang down and leaves the user's hands free to handle or hold the patient (e.g. a new-born baby) and direct the remote end of the second flexible tube into its mouth or elsewhere.

When the user sucks, upward distending of the diaphragm causes suction in the second compartment which causes the first non-return valve to open, thereby drawing air from the lowermost compartment into the second compartment, whereby suction is created in the second flexible tube to draw mucus or other fluid from the patient. The user can then release the suction applied to the first flexible tube, and can breathe freely, the diaphragm being urged towards its neutral state by its own elasticity, thus closing the first non-return valve to prevent return of air to the lowermost compartment and the second flexible tube so that fluid drawn from the patient cannot be expelled therefrom, the second non-return valve being opened by pressure building up in the second compartment to allow air to flow therefrom to the atmosphere. Repeated sucking and releasing of the first flexible tube therefore results in a build-up and maintenance of reduced pressure in the lowermost compartment, to continued drawing of fluid from the patient and discharging of it into that compartment.

If the cycle is repeated until fluid in the lowermost compartment reaches and passes through the first non-return valve it cannot reach the first flexible tube because of the barrier provided by the elastic diaphragm. Likewise, the elastic diaphragm provides a barrier to the user's breath (and particularly any germs therein) reaching the patient or even the fluid drawn off from the patient. However, the lowermost compartment is preferably transparent, to enable its contents to be viewed and repetition of the cycle discontinued before fluid in it reaches the first non-return valve.

The three compartments may be provided in one unified hollow body, in which case the whole extractor is disposable. Alternatively, the lowermost compartment may be formed by a hollow member detachable from a hollow body housing the uppermost and second compartments, in which case the lowermost compartment and the second fiexible tube may be disposable, a fresh hollow member with a fresh second flexible tube attached thereto being fitted to the hollow body for re-use thereof. Yet again, a hollow member forming a disposable lowermost compartment, possibly to be used for storing or transporting a patient's fluid sample for analysis or testing, may be connected to the uppermost compartment by a connector incorporating the second compartment, rom which connector branches the second flexible tube, and which connector or a part thereof is disposable with the second flexible tube.

An extractor in accordance with the invention may be made of inexpensive sterilisable plastics formed into simple components bonded together to form the compartments and secure the elastic diaphragm and the partition in place between them, with integral spigots to receive the flexible tubes, and with small holes with flaps forming the non-return valves.

A possible alternative to the diaphragm may be a bellows with one end closed and the other end open to the second compartment, the bellows either having an inherent ability to return to its collapsed state or being provided with spring means to effect such return when suction applied to the first flexible tube is released.

A preferred embodiment of the invention will now be described, by way of example only, with reference to the accompanying drawings in which:

FIG. 1 is a side elevation, substantially actual size, of a fluid extractor in accordance with the invention;

FIG. 2 is a vertical section corresponding to FIG. 1 to a larger scale;

FIG. 3 corresponds to FIG. 2 but shows the fluid extractor in a first operative condition; and FIG. 4 is a further enlarged fragmentary vertical section showing some detail in a second operative condition.

The fluid extractor shown in the drawings comprises three closed compartments 10, 11, 12 in vertical succession, the uppermost compartment 10 being separated from a second compartment 11 by an elastic diaphragm 13, the second compartment 11 being separated from the lowermost compartment 12 by a partition 14 containing a first non-return valve (or suction valve) 15 closed to air flow from the second compartment 11 to the lowermost compartment 12, a second non-return valve (or vent valve) 16 closed to air flow from the atomsphere to the second compartment 11, a first flexible tube (or sucking tube) 17 communicating at one end 18 with the upper region of the uppermost compartment 10, and a second flexible tube (or suction tube) 19 communicating at one end 20 with the upper region of the lowermost compartment 12, the diaphragm 13 being distended upwards (see FIG. 3) by suction, applied by mouth to the remote end 21 of the first flexible (sucking) tube 17 and through that tube to the uppermost compartment 10, from a neutral state (see FIG. 2) to which it returns when suction is released (see FIG. 2), air sucked from the lowermost compartment 12 through the suction valve 15 into the second compartment 11 being expelled through the vent valve 16 (see FIG. 4).

Thus, with the user's mouth (not shown) holding the remote end 21 of the sucking tube 17, by means of a mouthpiece 22, the extractor will hang down as shown in FIG. 3 and leaves the user's hands (not shown) free to handle or hold the patient (also not shown, but often a baby) and direct the remote end 23 of the suction tube 19 into its (the patient's) mouth or elsewhere.

When the user sucks, upward distending of the diaphragm 13 causes suction in the second compartment 11 which causes the suction valve 15 to open (see FIG. 3) thereby drawing air from the lowermost compartment 12 into the second compartment 11, whereby suction is created in the suction tube 19 to draw mucus or other fluid from the patient. The user can then release the suction applied to the sucking tube 17, and can breathe freely, the diaphragm 13 being urged towards its neutral state by its own elasticity, thus closing the suction valve 15 to prevent return of air to the lowermost compartment 12 and the second flexible tube 19 so that fluid drawn from the patient cannot be expelled therefrom, the vent valve 16 being opened (see FIG. 4) by pressure building up in the second compartment 11 to allow air to flow therefrom to the atmosphere. Repeated sucking and releasing therefore results in a build-up and maintenance of reduced pressure in the lowermost compartment 12, to draw fluid from the patient and discharge it into that compartment.

If the cycle is repeated until fluid in the lowermost compartment 12 reaches and passes through the suction valve 15 it cannot reach the sucking tube 17 because of the barrier provided by the elastic diaphragm 13. Likewise, the elastic diaphragm provides a barrier to the user's breath (and particularly any germs therein) reaching the patient or even the fluid drawn off from the patient.

The uppermost and lowermost compartments 10, 12 are formed by transparent hollow members 24, 25 snapping into a cylindrical connector 26 (which need not be transparent) with the partition 14 disposed centrally in it, whereby the working of the diaphragm 13 can be observed and the contents of the lowermost compartment 12 can be viewed, repetition of the cycle being discontinued bfore fluid reaches the suction valve 15.

Although the hollow members 24, 25 snap into the connector 26, so that the member 25 forming the lowermost compartment 12 could be detached for separate disposal or for storage of its contents after snapping on a lid (not shown), and although the end 20 of the suction tube 19, is a push-fit in a hole 27 in the cylindrical central member 26, so that the suction tube could be disposable, and replacement tubes 19 and members 25 provided, the use of simple inexpensive sterilisable plastics allows of the whole extractor being disposable for the best possible hygienic practics.

The diaphragm 13 is formed by a disc of thin latex sheet having a marginal portion 28 (see particularly FIG. 4) trapped between the snap-engaging portions of the member 24 forming the uppermost compartment 10 and the connector 26. The member 24 and the mouthpiece 22 are formed with spigots 29 on which the ends 18, 21 of the flexible sucking tube 17 are a push-fit.

The suction valve 15 consists of a hole in the partition 14 overlapped by a flexible flap 30 in the form of a disc with a hole at its centre for securing by a headed pin 31 which is a push-fit in a socket 32 in the partition; and the vent valve 16 consists of a hole in an upper cylindrical portion of the connector 26, incorporating the second compartment 11 encircled by an elastic band 33.

We claim:

1. A fluid extractor comprising at least three closed compartments in vertical succession, the uppermost compartment being separated from a second compartment by an elastic diaphragm, the second compartment being separated from the lowermost compartment by a partition containing a first non-return valve closed to air flow from the second compartment to the lowermost compartment, a second non-return valve closed to air flow from the atmosphere to the second compartment, a first flexible tube communicating at one end with the upper region of the uppermost compartment, and a second flexible tube communicating at one end with the upper region of the lowermost compartment, the diaphragm being distended upwards by suction, applied by mouth to the remote end of the first flexible tube and through that tube to the uppermost compartment, from a neutral state to which it returns when the suction is released.

2. A fluid extractor as in claim 1, wherein the remote end of the first flexible tube has a mouthpiece.

3. A fluid extractor as in claim 1 or claim 2, wherein the lowermost compartment is transparent.

4. A fluid extractor as in claim 3, wherein the uppermost compartment is transparent.

5. A fluid extractor as in claim 1, wherein said compartments are provided in one unified hollow body and the whole extractor is disposable.

6. A fluid extractor as in claim 1, wherein the lowermost compartment is formed by a hollow member detachable from a hollow body housing the uppermost and second compartments.

7. A fluid extractor as in claim 6, wherein the lowermost compartment and the second flexible tube are disposable.

8. A fluid extractor as in claim 1, wherein a hollow member forms a disposable said lowermost compartment connected to the uppermost compartment by a connector incorporating the second compartment, from which connector branches the second flexible tube, and which connector or a part thereof is disposable with the second flexible tube.

9. A fluid extractor as in claim 8, wherein the diaphragm is formed by disc of thin latex sheet having a marginal portion trapped between snap-engaging portions of a hollow member forming the uppermost compartment and the connector.

10. A fluid extractor as in claim 8 or claim 9, wherein the first non-return valve consists of a hole in the partition overlapped by a flexible flap in the form of a disc with a hole at its centre for securing by a headed pin which is a push-fit in a socket in the partition.

11. A fluid extractor as in claim 8, wherein the second non-return valve consists of a hole in an upper cylindrical portion of the connector incorporating the second compartment encircled by an elastic band.

12. A fluid extractor as in claim 1, further comprising a bellows with one end closed and the other end open to the second compartment, the bellows either having an inherent ability to return to its collapsed state or being provided with spring means to effect such return when suction applied to the first flexible tube is released.

13. A fluid extractor as in claim 1, wherein all the components except the diaphragm or bellows are made of inexpensive sterilisable plastics.

* * * * *